(12) United States Patent
Imperante et al.

(10) Patent No.: US 6,465,673 B1
(45) Date of Patent: Oct. 15, 2002

(54) SILICONE ROSINATE ESTERS

(75) Inventors: John Imperante, Somerville, NJ (US); Anthony J. O'Lenick, Jr., Dacula, GA (US)

(73) Assignee: Phoenix Research Corporation, Somerville, NJ (US)

( * ) Notice: Subject to any disclaimer, the term of this patent is extended or adjusted under 35 U.S.C. 154(b) by 0 days.

(21) Appl. No.: 10/157,554

(22) Filed: May 30, 2002

(51) Int. Cl.[7] .................................................. C07F 7/08
(52) U.S. Cl. ......................................... 556/437; 554/77
(58) Field of Search ............................. 556/437; 554/77

(56) References Cited

U.S. PATENT DOCUMENTS

| 4,724,248 A | | 2/1988 | Dexter |
| 5,136,063 A | | 8/1992 | O'Lenick |
| 5,417,967 A | * | 5/1995 | Kawamata et al. ..... 556/437 X |

* cited by examiner

*Primary Examiner*—Paul F. Shaver

(57) ABSTRACT

The invention relates to a series of novel propoxylated silicone rosin esters. This class of compounds provides unique solubility in organic solvents like iso-paraffin, and despite its lack of water solubility, provides an ability to couple water into anhydrous systems like lipsticks, minimizing the incompatibility that causes syneresis.

6 Claims, No Drawings

SILICONE ROSINATE ESTERS

BACKGROUND OF THE INVENTION

The invention relates to a series of novel propoxylated silicone rosin esters. This class of compounds provides unique solubility in organic solvents like iso-paraffin, and despite its lack of water solubility, provides an ability to couple water into anhydrous systems like lipsticks, minimizing the incompatibility that causes syneresis.

FIELD OF THE INVENTION

The field of the invention relates to a series of novel propoxylated silicone rosin esters. This class of compounds provides unique solubility in organic solvents like iso-paraffin, and despite its lack of water solubility, provides an ability to couple water into anhydrous systems like lipsticks, minimizing the incompatibility that causes syneresis.

ARTS AND PRACTICES

U.S. Pat. No. 5,136,063 issued to O'Lenick in August 1992 discloses a series of silicone esters that range in carbon length from C12 to C21. The compounds are claimed to provide outstanding softening and lubricating when applied to textiles and fibers. The patent states: "It is the object of the present invention to provide novel silicone based fatty ester compounds which are substantive to the surface of a fiber and other textile materials including cellulosic material and have increased solubility in fatty materials including mineral oil, fatty triglycerides and traditional fatty quaternary ammonium compounds. The compounds of the present invention render the lubricity, and hydrophobicity generally seen in silicone compounds, but because they are esterified with fatty groups have greater solubility in hydrocarbon oils as well as fatty materials than the traditional silicone compounds, which are insoluble in those materials."

As will become clear from the teaching of the current invention, the U.S. Pat. No. 5,136,063 did not recognized that only by selecting a propoxylated product, and the proper silicone polymer, and the proper fatty group, namely rosin acid, could a product be prepared that provides unexpected properties valuable properties in personal care applications, a very different application area than the textile art to which the U.S. Pat. No. 5,136,063 patent applies. These unexpected properties include solubility and homogeneity in iso-paraffin like iso-dodecane, ability to couple water into oil based systems, and the ability to provide personal care products like lipsticks and make up products that do not ooze oil, a phenomenon called syneresis.

THE INVENTION

Object of the Invention

It is the object of the present invention to provide a series of novel propoxylated silicone rosinate esters, that provides a unique solubility in organic solvents like iso-paraffin, and despite its lack of water solubility, provides an ability to couple water into anhydrous systems like lipsticks, minimizing the incompatibility that causes syneresis.

It is another object of the present invention to provide a process for providing cosmetic pigment to the skin, which comprises contacting the skin with an effective coloring amount of a pigmented product containing the novel propoxylated silicone rosinate esters.

SUMMARY OF THE INVENTION

The invention relates to a series of novel propoxylated silicone rosin esters, specifically dimethicone copolyol rosinate esters, which provide unique solubility in organic solvents like iso-paraffin, and despite its lack of water solubility, provides an ability to couple water into anhydrous systems like lipsticks, minimizing the incompatibility that causes syneresis this key component has been found to be critical to performance.

DETAILED DESCRIPTION OF THE INVENTION

The compounds of this invention are silicone propoxylated rosin esters made by the esterification of a propoxylated dimethicone copolyol compound with rosin acid or an oil that has a high concentration of erucic acid. The compounds of the present invention conform to the following structure;

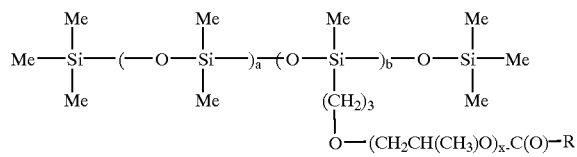

wherein;

Me is methyl;

R is derived from rosin acid;

a is an integer ranging from 1 to 20;

b is an integer ranging from 1 to 20;

x is an integer ranging from 5 to 20.

Rosin acid is a naturally occurring mixture of abietic acid, dehydroabietic acid, neoabietic acid, palustric acid, pimaric acid and isopimaric acid, derived from tall-oil.

These ringed structures, together with the silicone and polyoxypropylene in the molecule, provide the critical solubility to the products of the present invention. The fact that tall-oil is a renewable resource available from trees, makes these products all the more interesting to an environmentally conscious consumer. If ethylene oxide is present in the structure, the solubility in paraffin is lost. If a linear fatty acid is used rather than rosin the paraffin solubility is lost. If x is less than 5, the ability to complex water into the lipstick is lost. Only by properly selecting the molecules of the present invention is a functional product achieved.

PREFERRED EMBODIMENTS

In a preferred embodiment x is 5.

In a preferred embodiment x is 10.

In a preferred embodiment x is 15.

In a preferred embodiment x is 20.

In a preferred embodiment x is 7.

EXAMPLES

Rosin Acid

Rosin acid is a commercially available, naturally occurring mixture of abietic acid, dehydroabietic acid, neoabietic acid, palustric acid, pimaric acid and isopimaric acid, derived from tall-oil. These ringed structures, together with the silicone and polyoxypropylene in the molecule, provide the critical solubility to the products of the present invention. The fact that tall-oil is a renewable resource available from trees, makes these products all the more interesting to an environmentally conscious consumer.

Propoxylated Dimethicone Copolyols

Dimethicone copolyols are also called silicone glycols, and silicone surfactants. They are available form a variety of manufacturers. Siltech Corporation of Toronto Ontario Canada is a major one.

They conform to the following structure:

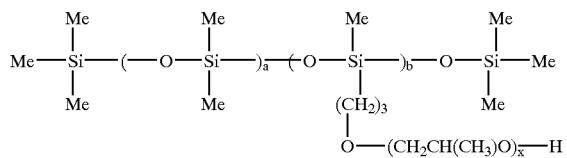

wherein;

Me is methyl;

a is an integer ranging from 1 to 20;

b is an integer ranging from 1 to 20;

x is an integer ranging from 5 to 20.

Examples 1–10

| Example | a | b | x |
|---|---|---|---|
| 1 | 1 | 10 | 5 |
| 2 | 5 | 4 | 5 |
| 3 | 10 | 10 | 10 |
| 4 | 5 | 6 | 20 |
| 5 | 20 | 7 | 20 |
| 6 | 15 | 20 | 7 |
| 7 | 9 | 4 | 15 |
| 8 | 10 | 10 | 20 |
| 9 | 20 | 10 | 5 |
| 10 | 9 | 5 | 3 |

General Reaction Conditions

The esterification can be carried out without catalyst; however, when no catalysts are reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240 C. under an inert nitrogen blanket. The nitrogen blanket to preserves the color. Preferred temperature range is between 180 and 210 C. Water is removed from the reaction, which is done using a nitrogen sparge or vacuum.

The reaction can be run with either a stoichiometric amount of the rosin acid, or a slight excess of either reactant.

Ester Examples

Example 11

Into a suitable round bottom, three neck flask equipped with a Dean Stark trap, a thermometer and a nitrogen sparge is added 300.0 grams of rosin acid, 0.25% by weight of the total batch charged of stannous oxylate and 730.0 grams of propoxylated dimethicone copolyol (example 1). The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is a clear liquid and is used without additional purification.

Examples 12

Example 11 is repeated only this time substituting the specified number of grams of the specified dimethicone copolyol.

| | Silicone Compound | |
|---|---|---|
| Example | Example | Grams |
| 12 | 2 | 545.0 |
| 13 | 3 | 797.0 |
| 14 | 4 | 1386.0 |
| 15 | 5 | 1531.0 |
| 16 | 6 | 593.0 |
| 17 | 7 | 1320.0 |
| 18 | 8 | 871.0 |
| 19 | 9 | 576.0 |
| 20 | 10 | 578.0 |

Applications Examples if ethylene oxide is present in the structure, the solubility in paraffin is lost. If a linear fatty acid is used rather than rosin the paraffin solubility is lost. If x is less than 5, the ability to complex water into the lipstick is lost. Only by selecting the molecules of the present invention is a functional product achieved.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A silicone rosin acid ester conforming to the following structure;

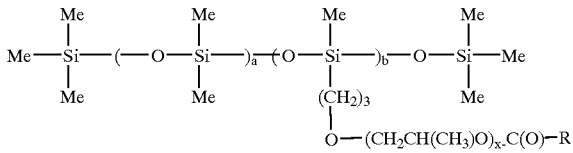

wherein;

Me is methyl;

R is derived from rosin acid;

a is an integer ranging from 1 to 20;

b is an integer ranging from 1 to 20;

x is an integer ranging from 5 to 20.

2. An ester of claim 1 wherein x is 5.

3. An ester of claim 1 wherein x is 10.

4. An ester of claim 1 wherein x is 15.

5. An ester of claim 1 wherein x is 20.

6. An ester of claim 1 wherein x is 7.

* * * * *